United States Patent
Hetzer et al.

(10) Patent No.: US 8,925,396 B2
(45) Date of Patent: Jan. 6, 2015

(54) METHOD AND SYSTEM FOR PARTICLES ANALYSIS IN MICROSTRUCTURE DEVICES BY ISOLATING PARTICLES

(75) Inventors: Petra Hetzer, Dresden (DE); Matthias Schaller, Moritzburg (DE); Dmytro Chumakov, Dresden (DE)

(73) Assignee: GLOBALFOUNDRIES Inc., Grand Cayman (KY)

( * ) Notice: Subject to any disclaimer, the term of this patent is extended or adjusted under 35 U.S.C. 154(b) by 957 days.

(21) Appl. No.: 12/725,688

(22) Filed: Mar. 17, 2010

(65) Prior Publication Data

US 2010/0242631 A1 Sep. 30, 2010

(30) Foreign Application Priority Data

Mar. 31, 2009 (DE) .......................... 10 2009 015 713

(51) Int. Cl.
| | | |
|---|---|---|
| *G01N 1/04* | (2006.01) | |
| *G01N 1/02* | (2006.01) | |
| *G01N 15/00* | (2006.01) | |
| *H01L 21/66* | (2006.01) | |

(52) U.S. Cl.
CPC ............ *G01N 1/02* (2013.01); *G01N 2001/028* (2013.01); *G01N 2015/0038* (2013.01); *H01L 22/12* (2013.01)
USPC ..................................... 73/864.31; 73/864.81

(58) Field of Classification Search
USPC ...................................................... 73/863.21
See application file for complete search history.

(56) References Cited

U.S. PATENT DOCUMENTS

| | | | |
|---|---|---|---|
| 5,746,829 A | 5/1998 | Matsunaga et al. ........... | 117/208 |
| 6,639,667 B1 * | 10/2003 | Gilbert et al. .................. | 356/301 |
| 6,858,851 B2 | 2/2005 | Tomimatsu et al. ...... | 250/442.11 |
| 6,861,648 B2 * | 3/2005 | Kley .............................. | 850/20 |
| 7,397,051 B2 | 7/2008 | Tomimatsu et al. ...... | 250/492.21 |
| 2005/0247886 A1 * | 11/2005 | Wang ........................ | 250/442.11 |
| 2006/0175192 A1 | 8/2006 | Lin ................................ | 204/194 |
| 2008/0307866 A1 * | 12/2008 | Hiroki et al. .................... | 73/105 |
| 2009/0045336 A1 | 2/2009 | Bloess et al. .................. | 250/307 |

FOREIGN PATENT DOCUMENTS

| | | | |
|---|---|---|---|
| DE | 103 47 969 A1 | 5/2005 | ............... B82B 3/00 |
| DE | 102005023872 A1 | 1/2006 | ............... G01N 1/32 |
| DE | 102007062272 A1 | 7/2008 | ............ G01N 21/94 |
| JP | 09085437 A | 3/1997 | ............. B23K 9/013 |

OTHER PUBLICATIONS

Translation of Official Communication from German Patent Office for German Patent Application No. 10 2009 015 813.1-52 dated Jun. 13, 2010.

* cited by examiner

*Primary Examiner* — Robert R Raevis
(74) *Attorney, Agent, or Firm* — Amerson Law Firm, PLLC (57) ABSTRACT

During the fabrication of microstructure devices, such as integrated circuits, particles may be analyzed by displacing or removing the particles from the device surface and subsequently performing an analysis process. Consequently, a well-defined measurement environment may be established after removal of the particles, which may be accomplished on the basis of nanoprobes and the like. Hence, even critical surface areas may be monitored with respect to contamination and the like on the basis of well-established analysis techniques.

22 Claims, 5 Drawing Sheets

METHOD AND SYSTEM FOR PARTICLES ANALYSIS IN MICROSTRUCTURE DEVICES BY ISOLATING PARTICLES

BACKGROUND OF THE INVENTION

1. Field of the Invention

Generally, the present disclosure relates to the field of manufacturing of microstructures, such as integrated circuits, and, more particularly, analysis techniques used for process monitoring and/or process control.

2. Description of the Related Art

In manufacturing microstructures, such as integrated circuits, micromechanical devices, opto-electronic components and the like, device features, such as circuit elements, are typically formed on an appropriate substrate by patterning the surface portions of one or more material layers previously formed on the substrate. Since the dimensions, i.e., the length, width and height, of individual features are steadily decreasing to enhance performance and improve cost effectiveness, these dimensions have to be maintained within tightly set tolerances in order to guarantee the required functionality of the complete device. Usually, a large number of process steps have to be carried out for completing a microstructure and, thus, the dimensions of the features during the various manufacturing stages have to be thoroughly monitored to maintain process control and to avoid further cost-intensive process steps owing to process tools that fail to meet the specifications in the various manufacturing stages.

For example, in sophisticated CMOS devices, a very large number of transistors, such as N-channel transistors and P-channel transistors, have to be formed in and above a semiconductor layer, wherein these transistor elements may comprise critical device features, such as gate electrodes and the like, which may have a critical dimension of approximately 50 nm and less in currently available products. In addition to steadily shrinking critical dimensions of the device features, new materials and process strategies may frequently have to be implemented in order to further enhance reliability, performance and cost-effectiveness. For example, the manufacturing of sophisticated field effect transistors requires new technologies due to significant limitations, which may be encountered by conventional planar transistor structures based on a gate dielectric material in the form of silicon dioxide, silicon oxynitride and other "conventional" dielectric materials, since these materials may typically result in significantly increased leakage currents, thereby resulting in undue heat generation which may not be compatible with requirements of many types of semiconductor devices. The limitations of well-established and well-approved dielectric materials in gate electrode structures have fueled new technology approaches, such as non-planar transistor configurations and/or sophisticated gate electrode structures. For instance, the scalability of planar transistor configurations may be significantly expanded by using complex gate electrode structures on the basis of high-k dielectric materials, which are to be understood as materials having a dielectric constant of 10.0 or higher, in combination with metal-containing electrode materials. Consequently, new materials, such as high-k dielectric materials and the like, may have to be implemented into the overall manufacturing flow, thereby requiring appropriate manufacturing techniques for depositing and patterning these materials. For this reason, also any new types of byproducts may be created during the processing of these materials, which may also require a thorough monitoring and investigation with respect to any interactions with other materials and manufacturing processes.

In still other approaches for enhancing transistor performance of complex integrated circuits, strain-inducing mechanisms may be implemented into the overall manufacturing flow for forming field effect transistors since a strained channel region of a silicon-based transistor may provide enhanced transistor performance due to a modified charge carrier mobility caused by the strained silicon-based material. For this purpose, strain-inducing semiconductor alloys, such as silicon/germanium, silicon/carbon and the like, may be incorporated into the active regions in a local manner, thereby selectively inducing a desired type of strain in individual transistor elements. Also in this case, sophisticated patterning and deposition techniques may be required which have to be applied within tightly set process tolerances in order to maintain overall device variability at a low level.

Similarly, after completing the circuit elements in a device level of complex integrated circuits, a contact level has to be formed, which may be considered as an interface between the circuit elements in the device level and a complex metallization system, which may be considered as a wiring fabric for connecting the individual transistor elements and other circuit elements in accordance with the required circuit function. Since at least in some device regions a very high density of individual circuit elements may have to be provided, the contact level may have to be formed on the basis of extremely complex deposition and patterning techniques in order to provide appropriate interlayer dielectric materials and patterning the same so as to form contact openings and filling the same with an appropriate metal-containing material. For example, the formation of contact openings in an interlayer dielectric material represents an extremely challenging manufacturing stage for very complex integrated circuits, which may, for instance, comprise densely packed memory areas and the like, since densely spaced contact openings with a high aspect ratio and with critical dimensions of approximately 100 nm and significantly less may have to be formed in a reliable and predictable manner. Consequently, the interaction of the different materials and processes may have a significant influence on the overall production yield in modern semiconductor facilities.

Moreover, typically, very complex metallization systems are required in modern semiconductor devices, wherein the complexity of the metallization system may reside in the fact that a plurality of metallization layers may have to be formed on top of each other, wherein complex material systems may also have to be provided in each of the metallization layers. For example, in modern integrated circuits including a very large number of circuit elements, typically, copper in combination with sophisticated dielectric materials, so-called low-k dielectric materials or ultra low-k (ULK) materials, may be used in order to reduce signal propagation delay in the metallization system. Due to copper's intrinsic characteristics, substantially not to form volatile etch byproducts on the basis of most of the well-established plasma assisted etch chemistries, typically, a process technique is applied in which a dielectric material may first be patterned so as to receive corresponding openings, such as trenches and via openings, which are subsequently filled with the copper material by electrochemical deposition techniques. However, due to the fact that copper may readily diffuse in silicon dioxide, silicon, a plurality of low-k dielectric materials and the like, a reliable confinement of the copper is required, since even minute amounts of copper diffusing to device regions such as active regions of transistors, may result in a significant change of the overall device characteristics. For this reason, complex barrier material systems may be provided, for instance, in the form of tantalum, tantalum nitride, ruthenium, titanium, titanium nitride and the like, which may provide a desired diffusion hindering effect and which may also provide the mechanical and chemical integrity of the copper material. Moreover, although copper-based interconnect structures may have a significantly low electrical resistivity compared to, for instance, aluminum, the reduced dimensions of the interconnect structures may nevertheless result in very high current densities, thereby also requiring strong interfaces between the copper material and the surrounding dielectric material that may have to be provided by the barrier material and corresponding cap materials in order to obtain the required performance with respect to electromigration. Consequently, in the complex manufacturing sequence for forming metallization layers, sensitive dielectric materials may have to be patterned based on appropriate plasma assisted etch processes, thereby also creating a plurality of etch byproducts, which may have a significant effect on the further processing of the device. Moreover, after patterning the sensitive dielectric material systems, one or more barrier materials, possibly in combination with seed materials, may have to be deposited by very sophisticated deposition techniques, wherein the process result may essentially depend on the surface conditions of the dielectric materials, corresponding defects and particles formed thereon and the like. Thereafter, the openings, such as trenches and via openings, are filled with the copper materials by very advanced electrochemical deposition techniques, which may require well-defined surface conditions of the previously deposited barrier/seed material in order to obtain the required bottom-to-top fill behavior without generating deposition-related irregularities, which may result in contact failure or reduced electrical performance. Thereafter, any excess material, such as copper in combination with barrier and seed materials, has to be removed, for instance by using polishing techniques and the like, wherein, frequently, an increased mechanical stress may be created, for instance, by a chemical mechanical polishing (CMP) process, which may result in the creation of high defect rate due to the nature of the polishing process and due to the fact that the sensitive dielectric material may typically exhibit a less mechanical stability compared to conventional dielectric materials, such as silicon dioxide and silicon nitride. For instance, in particular at the edge region of substrates, a significant material delamination may be observed, which may result in an increased degree of particle contamination of exposed surface areas of the substrate and of process tools and transport containers.

Hence, at the various stages during the fabrication of complex microstructure devices, such as integrated circuits, surface conditions, such as material characteristics, the presence of particles, their lateral size and characteristics and the like, have to be thoroughly monitored in order to maintain the process output of the various manufacturing stages within the tightly set tolerances. For this reason, a plurality of complex inspection and analysis techniques have been developed which may be applied during the various manufacturing stages. For example, frequent optical inspection techniques may be available for detecting particles, wherein, however, due to the restricted resolution of these techniques, the detection may be restricted to particles of moderately large size so that critical device areas, such as areas having a pronounced surface topography, for instance due to the presence of trenches, contact openings and the like, may not yield meaningful results since typically the lateral dimensions of these device features may be significantly smaller compared to the wavelength of the optical inspection tool. In other cases, very sensitive and efficient analysis techniques may be provided on the basis of infrared spectroscopy using an interference modulated probing beam, which after interaction with a material of interest may be efficiently converted into a spectrum by Fourier transformation that in turn may be analyzed with respect to chemical characteristics of the material of interest. Although this technique may provide fast and accurate analysis results, the spatial resolution thereof is less compared to other optical inspection techniques so that only an average characterization of the chemical characteristics may be obtained. With other sophisticated analysis techniques, such as AFM (atomic force microscopy), the size and shape of particles in the sub micrometer range may be detected by scanning a corresponding surface portion wherein, however, other characteristics, such as chemical characteristics, chemical bonds within the material of interest and the like, may be very difficult to be determined on the basis of these techniques. Similarly, electron microscopy in transmission mode (TEM) may be efficiently applied in order to determine the presence and size and shape of particles, even provided on surface areas having a very pronounced topography, for instance within contact openings and the like, wherein, however, other characteristics, such as chemical characteristics and the like may be difficult to be identified on the basis of electron microscopy. Moreover, very sophisticated sample preparation may be required which may typically necessitate the destruction of the sample of interest. Moreover, in many of these sophisticated analysis techniques, the difficulty in determining characteristics of particles of interest may stem from the fact that the local neighborhood of the particle may also have a significant influence on the measurement results so that the response of the particle of interest may be difficult to be extracted from the response of the neighboring material.

The present disclosure is directed to various methods and systems that may avoid, or at least reduce, the effects of one or more of the problems identified above.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Generally, the present disclosure relates to techniques and systems in which a material sample of a microstructure device, such as a semiconductor device during various manufacturing stages, may be analyzed with an increased signal-to-noise ratio by "establishing" an appropriate measurement environment for the material sample of interest, such as a particle, wherein the measurement environment may have a well-defined response to a given analysis technique, thereby enabling an efficient detection of material characteristics, such as chemical composition, chemical bonds and the like. Consequently, by providing a defined measurement environment, the material sample, such as a particle, may be "isolated" from its neighborhood in the microstructure device, which may conventionally interfere with a signal obtained from the particle or material of interest. In some illustrative aspects disclosed herein, the isolation of the material sample or particle of interest may be accomplished by removing the particle from the surface area under consideration and subsequently performing an analysis process based on any appropriate technique. For instance, the removal process may be performed on the basis of a probe, such as a nanoprobe and the like, which may provide a desired spatial resolution so that an efficient material analysis may be accomplished during the various manufacturing stages in forming microstructure devices, such as integrated circuits and the like. In other cases, at least a displacement of the particle of interest may be initiated within or on the surface area of interest, for instance by positioning the particle of interest within a "measurement environment," i.e., a reference region, which may be subjected to the analysis technique prior to positioning one or more particles therein. In some illustrative embodiments disclosed herein, the actual analysis process may be performed after removal of the particle when still adhering to the probe, thereby enabling a fast and efficient detection of characteristics, such as chemical composition, chemical bonds within the material of interest and the like, wherein the appropriate analysis technique may be used independently of the microstructure device, that is, even very sophisticated analysis techniques, such as electron microscopy and the like, which may require a sample preparation, may be applied as a "non-destructive" analysis technique since the microstructure device under consideration may substantially not be affected by the further analysis process. In other cases, fast and efficient analysis techniques such as FTIR and the like may be used, thereby providing for an "inline" monitoring of material characteristics, for instance of contaminating particles and the like, wherein the interaction between the probe and the microstructure device may be restricted to predefined test areas, thereby reducing influence on other device areas at a low level. Furthermore, since the size of the probe may be appropriately adapted to the device features of the microstructure device, a determination of particle characteristics may be accomplished in sophisticated device topographies, for instance within trenches and contact openings of sophisticated metallization systems and the like, wherein the removal of the particle of interest and the subsequent analysis thereof enable the application of techniques that may basically have a spatial resolution that may be significantly greater compared to critical dimensions as defined by the device topography under consideration. Consequently, even techniques such as FTIR and optical inspection techniques may be efficiently used, although a corresponding wavelength of the probing beams of these techniques may be significantly longer compared to the critical dimensions under consideration. Furthermore, due to the mechanical displacement of the particles of interest, even an accumulation of material may be accomplished, thereby also increasing the amount of response to a probing beam of the subsequent analysis technique.

One illustrative method disclosed herein relates to analyzing a material sample of interest that is positioned on a surface of a microstructure device. The method comprises removing the material sample from the surface by contacting the material sample with a probe. Moreover, the method comprises performing an analysis process with the material sample remote from the surface.

A further illustrative method disclosed herein comprises detecting a particle on the surface of a microstructure device wherein the particle has a local neighborhood in the surface. The method further comprises obtaining reference measurement data from a defined measurement environment and positioning the particle in the defined measurement environment without the local neighborhood. Additionally, the method comprises performing an analysis process on the particle in the defined measurement environment on the basis of the reference measurement data.

One illustrative particle treatment system disclosed herein comprises a probe for contacting a surface of a patterned microstructure device. The system further comprises a substrate holder for receiving the microstructure device and a scan system that is operatively connected to the probe and the substrate holder, wherein the scan system is configured to position the probe on a surface portion of the microstructure device. Moreover, the system comprises a particle pickup unit operatively connected to at least one of the probe and the substrate holder, wherein the particle pickup unit is configured to initiate adherence of a particle of interest to the probe and to remove the particle from the surface.

BRIEF DESCRIPTION OF THE DRAWINGS

The disclosure may be understood by reference to the following description taken in conjunction with the accompanying drawings, in which like reference numerals identify like elements, and in which:

FIG. 1$a$ schematically illustrates a cross-sectional view of a microstructure device comprising a patterned surface including particles of interest, such as contaminants and the like, which may be displaced within the surface of the device on the basis of a probe in order to position one or more particles within a well-defined measurement environment, according to illustrative embodiments;

FIG. 1$b$ schematically illustrates a microstructure device having a surface topography, for instance representing a metallization system of a semiconductor device, wherein a probe may be brought into contact with particles at various surface areas, according to illustrative embodiments;

FIG. 1$c$ schematically illustrates a cross-sectional view of the microstructure device and of a probe that "picks" one or more particles of interest so as to perform a further analysis process remote from the surface, according to illustrative embodiments;

FIGS. 1$d$-1$g$ schematically illustrate cross-sectional views of the microstructure device in contact with various probes for efficiently removing one or more particles of interest from the surface for further analysis, according to further illustrative embodiments;

FIG. 1$h$ schematically illustrates a particle treatment system in which one or more particles may be removed from a microstructure device and may be analyzed by using at least a portion of a corresponding probe as a measurement environment, according to illustrative embodiments; and FIG. 1$i$ schematically illustrates the particle treatment system according to still further illustrative embodiments in which an optical detection method may be applied after removing one or more particles without manipulating the corresponding probe.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures, systems and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

The present disclosure generally relates to techniques and particle treatment systems in which a removable material sample or a particle may be exposed to an analysis process on the basis of any appropriate probing beam or radiation, wherein the particle may be physically displaced on the basis of a probe in order to enhance overall performance of the subsequent analysis process. In some illustrative embodiments disclosed herein, the displacement of the particle of interest may be associated with a removal thereof from a corresponding surface of a microstructure device, thereby efficiently isolating the particle from its local neighborhood in the microstructure device which may conventionally significantly interfere during a corresponding analysis process. In other cases, the particle may be displaced within the microstructure device in order to provide enhanced measurement conditions, for instance with respect to background noise and the like, thereby also contributing to an enhanced measurement sensitivity. As previously explained, a plurality of metrology systems may be available in which a contact of a probe with a surface of interest may be used to determine characteristics of a surface topography or even of extended surface areas with respect to physical characteristics, such as response to excitation on the basis of ultrasound and the like. However, these techniques may be less efficient in detecting chemical characteristics, chemical bonds, the optical appearance and the like with the desired high spatial resolution, in particular when the material of interest may represent a particle that has a more or less pronounced adhesion to the underlying surface. Consequently, according to the principles disclosed herein, an appropriate probe, such as a nanoprobe, formed of any appropriate material, such as conductive materials, dielectric materials and the like, carbon nanocubes, appropriately prepared optical fibers, if moderately coarse spatial resolution is sufficient, and the like, may be used in combination with a scan system for accessing a desired surface area of a microstructure device in order to allow contact with the particle of interest. Consequently, a desired high spatial resolution may be achieved by selecting an appropriate shape and configuration of the probe, for instance, having a tip portion, a shovel-like portion, a screw-like configuration and the like, in order to displace or remove the particle of interest due to the interaction with the probe. Consequently, the configuration and the size of the probe may also be adjusted with respect to the surface topography of the microstructure device under consideration so that any type of device features may be efficiently probed, such as contact openings, trenches and the like, which, in conventional strategies, may be difficult to be probed without using destructive techniques. For example, critical areas, such as the bottom of contact openings and via openings, may be probed in view of contaminants or any other particles, and these particles may be displaced, for instance, these particles may be positioned at extended surface areas that may be accessible to efficient analysis techniques, or particles may be completely removed from the microstructure device and may be positioned in a corresponding measurement environment. For instance, one or more particles of interest may be removed upon interaction with the probe, which may then act as a part of the measurement environment so that an analysis process may be performed without removing the particles of interest. In this manner, a fast and efficient application of a plurality of measurement techniques, such as AES (Auger electron spectroscopy), SIMS (secondary ion mass spectroscopy), FTIR (Fourier transformed infrared spectroscopy), Raman spectroscopy, TEM (transmissive electron microscopy) and the like, may be applied subsequent to the removal of the particle.

Figure 1A:
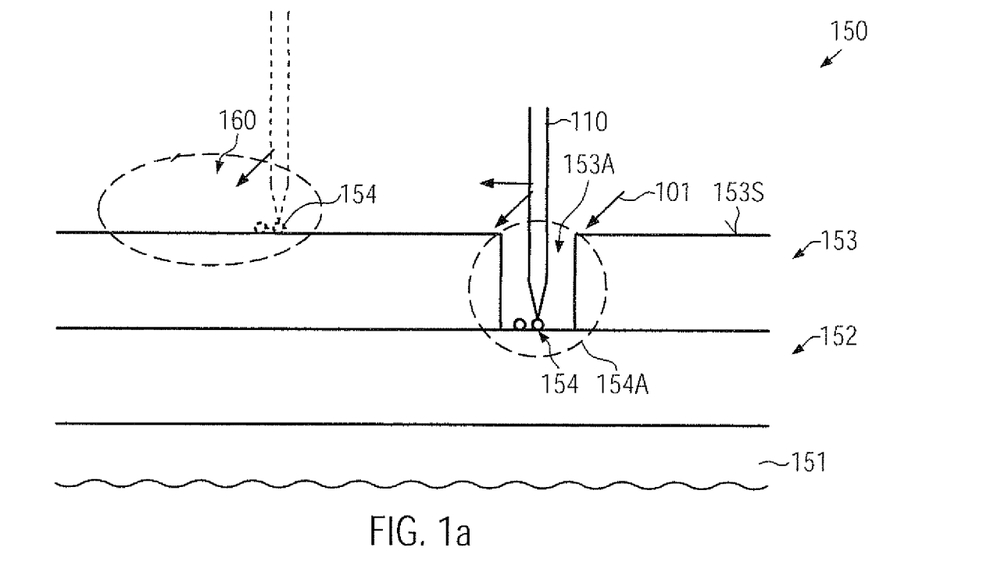

FIG. 1a schematically illustrates a cross-sectional view of a microstructure device 150 comprising a substrate 151 above which may be formed one or more layers 152, 153. For example, the device 150 may represent any microstructure device that may be formed on the basis of microelectronic and micromechanical techniques, such as semiconductor devices and the like. For example, the substrate 151 may represent a carrier material for forming thereabove a semiconductor material, in and above which circuit elements may be formed. For example, the layer 152 may represent a device level including any such circuit elements which, for convenience, are not shown in FIG. 1a. Moreover, the layer 153 represents any material layer, such as a dielectric layer, possibly in combination with additional materials, such as barrier materials and the like, in which a surface topography may be provided. For instance, a surface 153S may represent the surface of the device 150 according to the manufacturing stage shown in FIG. 1a and may comprise one or more device features 153A, such as an opening and the like. The device feature 153A may have a critical dimension, for instance, the lateral extension in FIG. 1a, of several tenths of nanometers or even less to several hundred nanometers and higher, depending on the overall design rules for the device 150 and the corresponding level represented by the material layer 153.

With respect to manufacturing strategies for forming the microstructure device 150, it is to be appreciated that any appropriate manufacturing regime may be applied, for instance as previously explained, as required by the device and process requirements. As explained above, during the manufacturing sequence, specific particles may deposit on the surface 153S, such as contaminants or any other material samples that may have a significant influence on the further processing of the device 150 and also on the finally obtained performance. For example, particles 154 may be positioned at the bottom of the opening 153A and corresponding characteristics thereof, such as the chemical composition, chemical bonds, size and shape and the like, may have to be determined. As previously discussed, the particles 154 may typically be positioned in a local neighborhood 154A, which may be understood as the materials surrounding the particle 154 and which may also respond to a probing beam 110 when applying a specific analysis technique. For example, an optical beam may be used wherein, typically, the spatial resolution thereof may be significantly lower so that the neighborhood 154A as a whole may respond to the beam so that specific response of the particles 154 may be difficult to be extracted. In the embodiment shown, a probe 110 of a particle treatment system (not shown in FIG. 1a), which will be described later on in more detail, may have an appropriate configuration, i.e., size and shape, in order to probe the opening 153A, thereby also enabling a contact with the particles 154. As will be described later on in more detail, a plurality of probes may be available or may be appropriately fabricated so as to be brought into contact with the surface 153S. Upon contact with the probe 110, one or more of the particles 154 may adhere to the probe 110, which may then be moved so as to displace the one or more particles 154 which, in the embodiment shown, may result in the positioning of the one or more particles 154 in a region 160, which may be accessible by the probing beam 110. Consequently, the region 160 may be probed by the beam 110 without the particle 154, thereby obtaining reference data, which may then be efficiently used upon probing the region 160 when containing the one or more particles 154. Hence, in this manner, the region 160 may be considered as a well-defined measurement environment with respect to an analysis technique using the probing beam 110. For example, the probing beam 110 may represent an optical beam, an infrared beam and the like, in order to obtain desired information with respect to some characteristics of the particle 154.

Figure 1B:
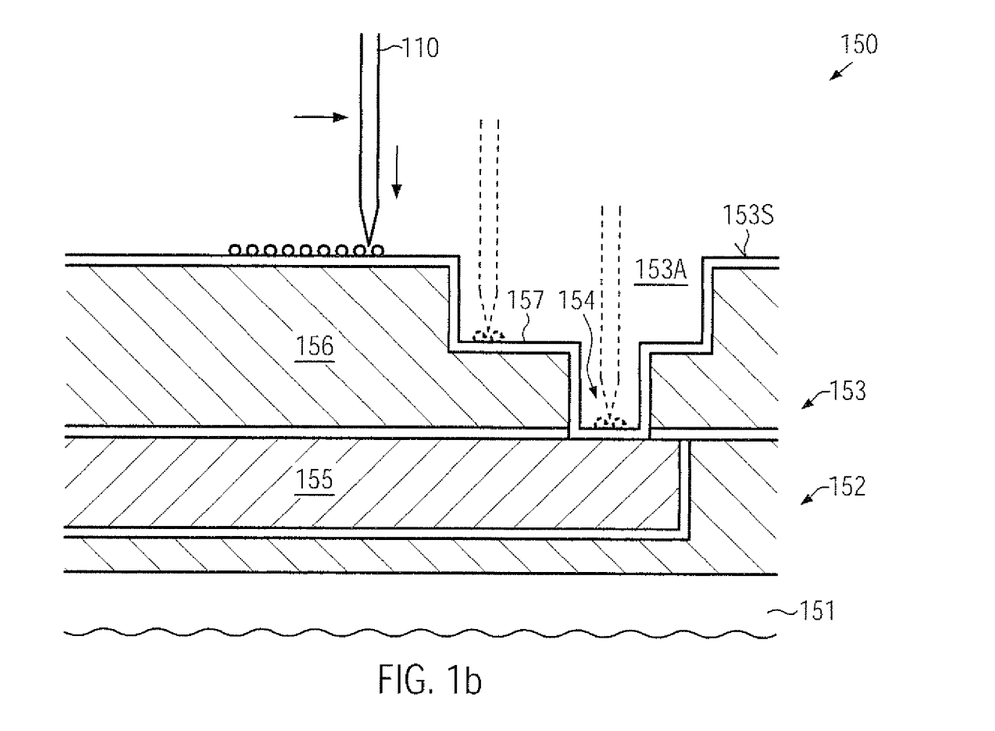

FIG. 1b schematically illustrates the microstructure device 150 according to further illustrative embodiments in which the microstructure device 150 may represent a semiconductor device. In the embodiment shown, the layers 152, 153 may represent metallization layers of a metallization system of the device 150, wherein the metallization layer 152 may comprise a metal region 155, for instance in the form of a copper-based metal region, which may be embedded in a dielectric material, such as a low-k dielectric material and the like. Similarly, the layer 153 may represent a metallization layer comprising a dielectric material 156, such as a low-k dielectric material, a ULK material and the like, in which the opening 153A may represent a trench and/or a via opening in accordance with the overall design rules of the metallization layer 153. As is illustrated, also in this case, particles 154 may be contacted by the probe 110 at any desired surface area, for instance substantially horizontal portions, or within the opening 153A, as may be required by the overall metrology strategy to be used. With respect to contacting the particles 154 with the probe 110 in order to displace or remove the particles, the same criteria may apply as previously explained, or as will be explained later on in more detail. For example, as previously explained, the metallization layer 153 may comprise a complex barrier/seed material system 157, which may significantly affect the further processing, for instance the filling in of copper material on the basis of electrochemical deposition techniques, wherein the presence of the particles 154 may represent an important factor of the finally obtained metal regions, for instance with respect to defectivity and the like. Consequently, the surface area within the opening 153A represents a critical area, since here sophisticated deposition conditions may be encountered during the deposition of the system 157 and during the subsequent deposition of a metal, such as copper. Thus, the principles disclosed herein may provide the possibility of detecting, displacing and finally analyzing the particles 154 within the opening 153A.

Figure 1C:
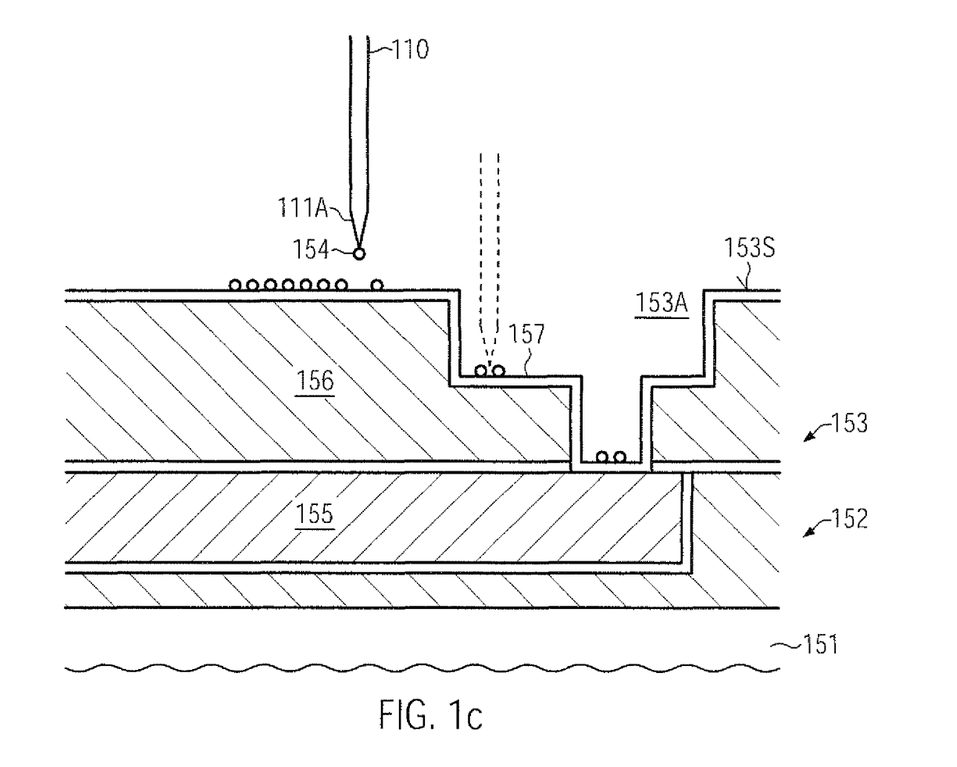

FIG. 1c schematically illustrates the microstructure device 150 in a stage in which one or more of the particles 154 may be displaced by the probe 110. For this purpose, the particle 154 may be contacted by the probe 110 and may adhere to the probe 110, which may be subsequently moved so as to remove the particle 154 from the surface 153S. To this end, a tip 111A of the probe 110 may be appropriately configured to apply, for instance, mechanical pressure to the particle 154 in order to achieve the desired degree of adhesion.

Figure 1D:
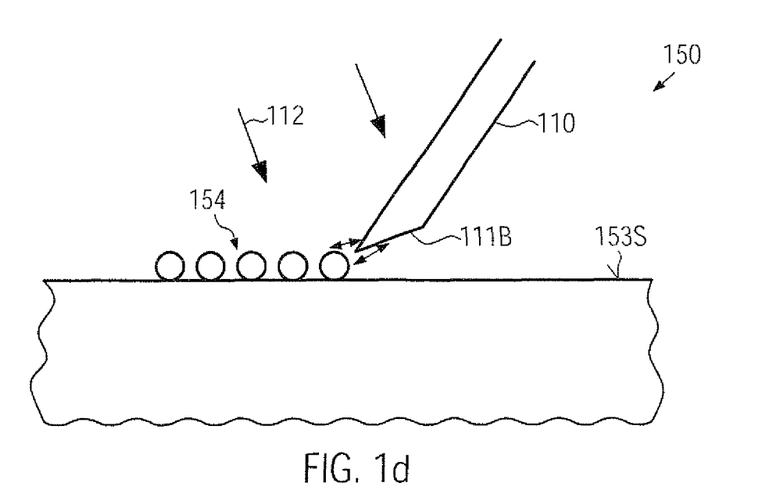

FIG. 1d schematically illustrates the device 150 during a process for removing one or more of the particles 154, wherein adhesion to an end portion 111B of the probe 110 may be initiated by appropriately preparing the end portion 111B and/or a local environment of the particles 154. For example, in some illustrative embodiments, at least the end portion 111B may be conditioned, for instance by applying a chemical agent and the like, in order to enhance adhesion of the particles 154. To this end, prior to contacting the surface 153S, the end portion 111B may be brought into contact with an appropriate chemical, for instance provided in the form of a bath and the like, or the chemical agent may be applied by any other appropriate deposition technique, such as spraying and the like. In still other cases, an electrochemical reaction may be initiated so as to enhance adhesion of the particles 154. For this purpose, an appropriate electrolyte may be introduced into the environment 112 and a corresponding voltage may be generated, for instance via the portion 111B. In still other cases, a chemical reaction between the end portion 111B, which may have formed thereon an appropriate chemical agent or which may per se allow a reaction with the particles 154 or at least portions thereof, may be initiated or enhanced by establishing an appropriate environment, for instance by radiation, heat, temperature reduction, plasma and the like.

Figure 1E:
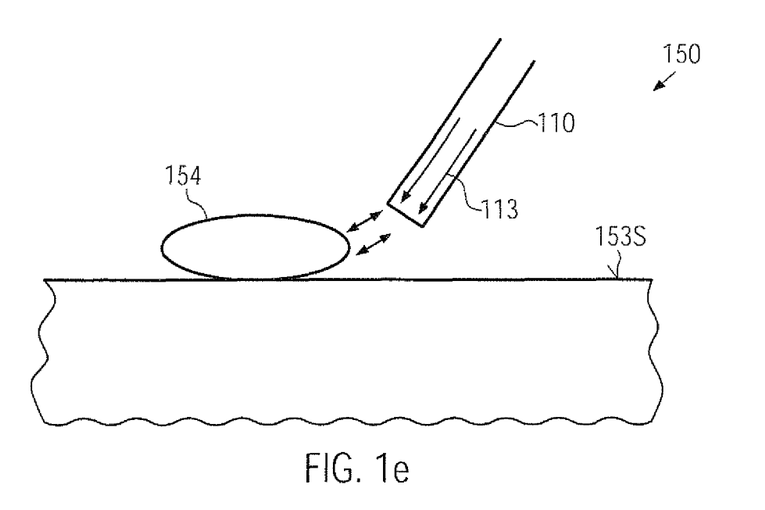

FIG. 1e schematically illustrates the device 150 where the probe 110 may comprise a fiber, such as an optical fiber, if the lateral size thereof is appropriate for scanning the surface 153S of the structure 150. For example, if particles 154 of a pronounced size may have to be displaced or removed, the probe 110 may be provided on the basis of an optical fiber material wherein, if desired, even optical energy 113 may be supplied via the fiber 110. Hence, light energy may be directly provided at the particle 154 so as to initiate a chemical or any other reaction for enhancing adhesion to the probe 110.

Figure 1F:
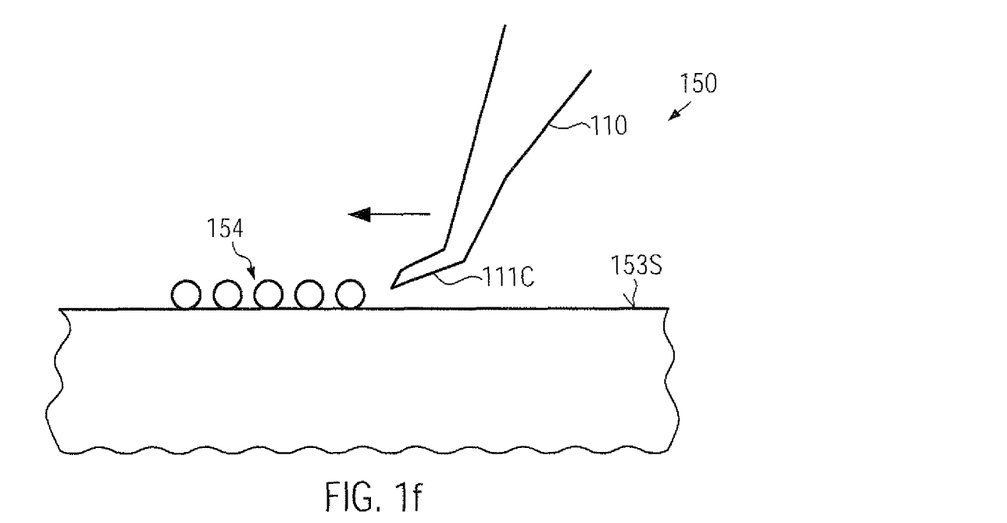

FIG. 1f schematically illustrates the microstructure device 150 when being contacted by the probe 110, which may be configured so as to "scratch" the surface 153S in order to release one or more of the particles 154 and displace or remove them for a subsequent analysis. For example, the end portion 111C may have a shovel-like configuration, thereby providing a moderately large surface area for accommodating one or more of the particles 154. For instance, in this manner, a certain degree of material accumulation may be accomplished on the end portion 111C, which may further enhance overall measurement sensitivity during the subsequent analysis process.

Figure 1G:
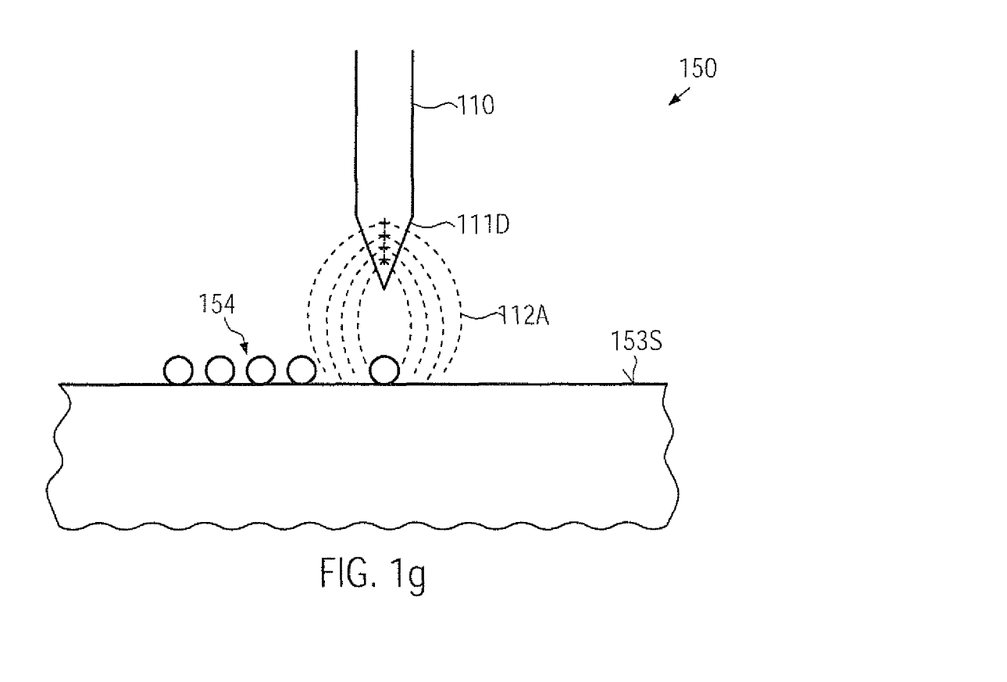

FIG. 1g schematically illustrates the microstructure device 150 with the probe 110, the end portion 111D of which may be appropriately configured so as to establish an electrostatic field 112A in order to interact with one or more of the particles 154. Consequently, depending on the type of material, enhanced adhesion may be accomplished by means of the electrostatic field 112A so as to allow the removal of one or more of the particles 154.

It should be appreciated that any other contact regime between the probe 110 and the particles 154 may be applied, depending on the overall surface conditions, the required spatial resolution, the requirement for enhanced integrity of the neighborhood of the particles 154 and the like. Furthermore, a plurality of available probes, for instance as may be used for AFM tools, may be advantageously used for displacing or removing the particles 154. In other cases, appropriate probes may be formed, for instance on the basis of micromechanical or microelectronic manufacturing techniques. For this purpose, appropriate substrate materials, such as silicon, silicon nitride, silicon dioxide and the like, possibly in combination with appropriate material layers, such as conductive or insulating materials, may be used and may be patterned in a three-dimensional manner in order to obtain the probe in accordance with any desired shape and size, possibly in combination with an appropriate cantilever in order to connect to a scan system for appropriately positioning and moving the probe 110.

Figure 1H:
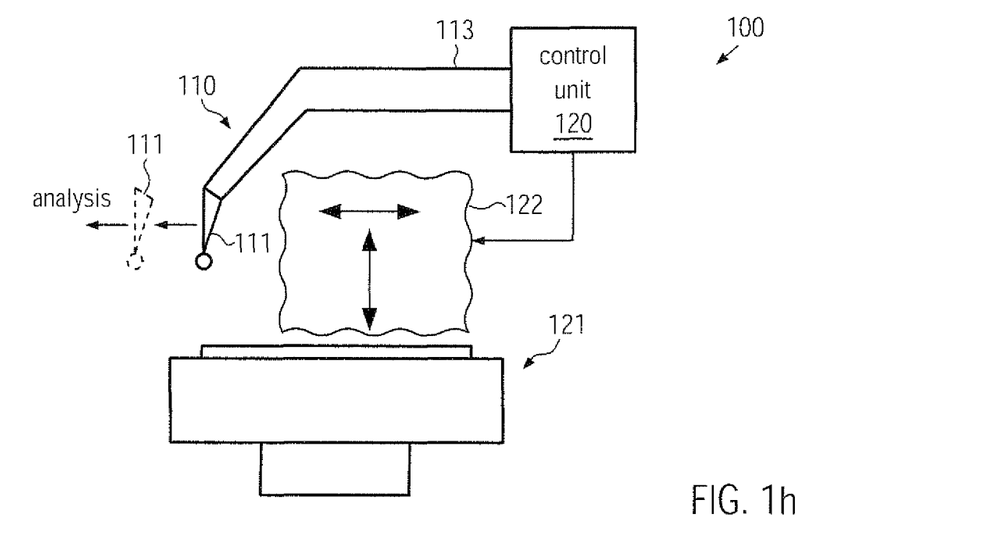

FIG. 1*h* schematically illustrates a particle treatment system 100 comprising a substrate holder 121 which may be appropriately configured in order to receive a substrate including one or more microstructure devices, such as the device 150, as previously described with reference to FIGS. 1*a*-1*g*. Furthermore, the system 100 may comprise a holder or cantilever 113 that is mechanically connected to the probe 110, which in turn may comprise an appropriate end portion 111, as previously explained. The cantilever 113 may be connected to a control unit 120, which may include any appropriate drive and control assembly for adjusting parameters, such as down pressure of the probe 110, establishing an electrostatic field and the like. Furthermore, the control unit 120 may further be configured to act as a scan system that may enable any relative movement between the substrate holder 121 and the probe 110, as may be required for scanning the end portion 111 across a specific surface area. In other illustrative embodiments, a separate scan unit 122 may be provided which may be operatively connected to the substrate holder 121 and/or the probe 110 so as to provide the desired scan motion. For example, the system 100 may comprise similar components as may typically be used in an AFM tool, when a spatial resolution in the sub micrometer range is desired.

During the operation of the particle treatment system 100, a substrate may be positioned on the substrate holder 121 and the probe 110 may be placed above the substrate at any desired position. For example, a region of interest may be determined in advance and the probe 110 may be positioned in the region of interest and a corresponding scan motion may be initiated by contacting the corresponding surface in order to "collect" one or more of the particles of interest. In other illustrative embodiments, the probe 110 may be used as a detector for identifying particles, for instance by measuring a surface roughness of a region of interest and identifying a pronounced protrusion on the basis of a the surface topography, which may then be identified as a particle. In this case, the tool 100 may transit into a displacement or removal operating mode, for instance by initiating an interaction with the detected particle, for instance on the basis of any of the above-identified strategies. After interaction with the surface, the particle of interest, which may adhere to the end portion 111, may be displaced, as previously described with reference to FIG. 1*a*, or may be removed from the surface under the control of the scan unit 122 and/or the control unit 120. Thereafter, an analysis process may be performed, for instance on the basis of any of the above-identified measurement techniques. For example, in some illustrative embodiments, the end portion 111 may be used as part of the well-defined measurement environment, for instance by using the end portion 111 and positioning the same within an appropriate environment, such as a process chamber and the like. For this purpose, reference data may be obtained from the end portion 111 in a "non-contaminated" state, for instance prior to removing one or more particles, so that a difference of two measurements may be determined and may be used for quantitatively estimating one or more characteristics of the particle of interest.

Figure 1I:
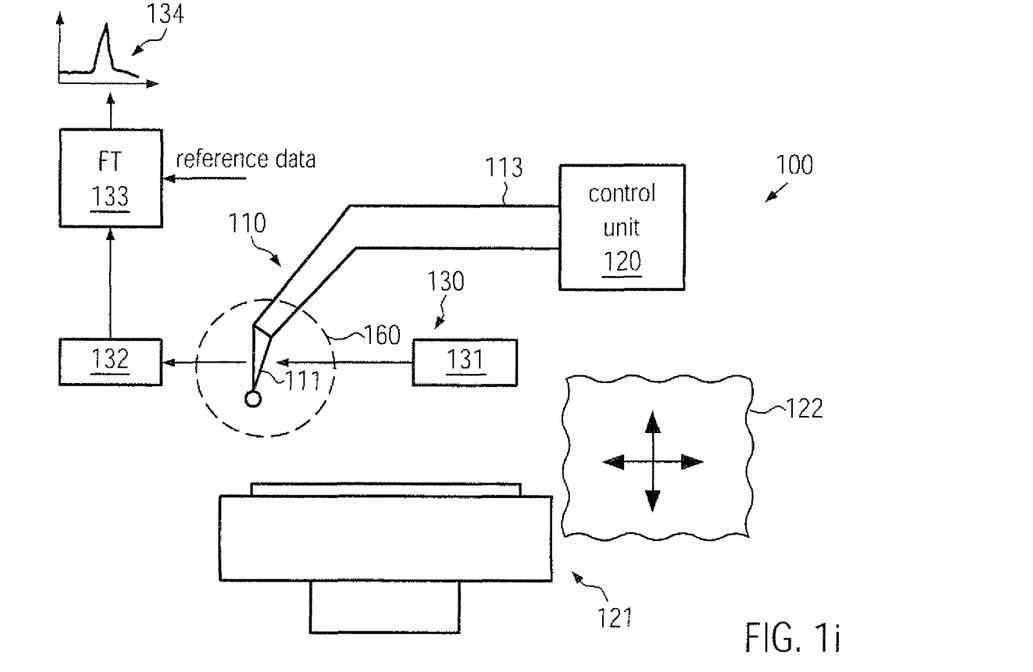

FIG. 1*i* schematically illustrates the system 100 according to further illustrative embodiments in which, additionally, an analysis system 130 may be provided. The analysis system 130 may comprise any appropriate components for determining one or more characteristics of the particles of interest. In the embodiment shown, the system 130 may represent an optical measurement system, for instance configured to perform a Fourier transformed infrared spectroscopy (FTIR), in which chemical composition, chemical bonds and the like may be efficiently determined on the basis of measurement spectra. For instance, a radiation source 131, which may provide an infrared beam that may be modulated by interference, may be positioned so as to enable irradiation of the end portion 111, while a detector 132 may be appropriately positioned so as to receive at least a portion of the beam of the radiation source 131 after interacting with the end portion 111. Furthermore, a data processing unit 133 may be provided, which may receive the measurement data in the form of interferograms and may perform a Fourier transformation to provide corresponding spectra 134, which may contain information about one or more material characteristics of interest. For instance, the amount and the type of specific atomic species, the presence and the status of specific chemical bonds and the like may be determined on the basis of the spectra 134. Furthermore, the data process unit 133 may receive reference data which may be obtained, for instance, from the portion 111 prior to contacting the surface portion of interest. Consequently, the system 130 may thus comprise the measurement environment 160 of well-defined status, thereby enabling an efficient evaluation of material characteristics since the reference data may be "subtracted" or otherwise be used for extracting the relevant information from measurement spectra 134. It should be appreciated that, in some illustrative embodiments, the end portion 111 may be replaced after a corresponding contact with the surface of interest, while in other cases an appropriate cleaning process may be performed, for instance by exposing the end portion 111 to any appropriate ambient, such as a wet chemical ambient, a plasma assisted ambient and the like, in order to remove at least significant portions of the preceding "contamination." It should be appreciated that a minor degree of contamination may readily be taken into consideration by obtaining corresponding reference data prior to an actual measurement process.

As a result, the present disclosure provides systems and techniques for enhancing the efficiency of characterization of particles positioned on a microstructure device by "isolating" particles from the immediate neighborhood by displacing or removing the particles and subsequently performing a measurement process.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of analyzing a material sample of interest formed on a surface of a microstructure device, the method comprising:
removing said material sample from a first position on said surface of said microstructure device by contacting said material sample with a probe;
moving said removed material sample to a second position on said surface of said microstructure device that is spaced apart from said first position; and
after moving said removed material sample to said second position, performing an analysis process on said removed material sample while said removed material sample is in said second position.

2. The method of claim 1, wherein said microstructure device comprises a surface topography that defines lateral dimensions of approximately 1 µm or less.

3. The method of claim 1, wherein removing said material sample comprises contacting said surface with said probe and mechanically displacing said material sample by said probe.

4. The method of claim 1, wherein removing said material sample comprises initiating adhesion of said material sample to said probe by establishing an electric field between said probe and said material sample.

5. The method of claim 1, wherein removing said material sample comprises locally applying pressure to said material sample by said probe substantially without contacting said surface.

6. The method of claim 1, wherein removing said material sample comprises providing an electrochemical environment at least locally at said material sample.

7. The method of claim 1, wherein removing said material sample comprises irradiating said material sample so as to enhance adhesion to said probe.

8. The method of claim 1, wherein performing said analysis process comprises analyzing said material sample in the presence of at least a portion of said probe.

9. The method of claim 8, wherein performing said analysis process comprises obtaining reference data from said at least a portion of said probe in the absence of said material sample and analyzing said material sample on the basis of said reference data.

10. The method of claim 1, wherein performing said analysis process comprises removing at least a portion of said material sample from said probe and analyzing said at least a portion of said material sample.

11. The method of claim 1, wherein performing said analysis process comprises performing at least one of an Auger electron spectroscopy, a secondary ion mass spectroscopy, a Fourier transformed infrared spectroscopy, a Raman spectroscopy and an electron microscopy.

12. The method of claim 1, wherein said material sample has a size of approximately 100 nm or less.

13. The method of claim 1, wherein said surface is a surface of a metallization layer of a semiconductor device.

14. The method of claim 1, wherein performing said analysis process on said removed material sample comprises determining at least one physical characteristic of said material sample.

15. A method, comprising:
detecting a particle at a first position on a surface of a microstructure device, said particle having a local neighborhood in said surface;
obtaining reference measurement data from a defined measurement environment on said surface of said microstructure device, said defined measurement environment being outside of said local neighborhood;
moving said particle from said first position on said surface of said microstructure device to a second position on said surface of said microstructure device and in said defined measurement environment, said second position being spaced apart from said first position; and
after moving said particle from said first position to said second position, performing an analysis process on said particle in said defined measurement environment on the basis of said reference measurement data.

16. The method of claim 15, wherein moving said particle to said second position in said defined measurement environment comprises contacting said particle with a probe.

17. The method of claim 16, wherein moving said particle to said second position in said defined measurement environment comprises removing said particle from said surface.

18. The method of claim 16, wherein contacting said particle with a probe comprises initiating an interaction between said probe and said particle by at least one of applying a mechanical pressure, scratching said local neighborhood, providing a chemical adhesive on said probe, applying an electric field, establishing an electrochemical environment, controlling a temperature of said local neighborhood and applying radiation energy.

19. The method of claim 15, wherein said microstructure device comprises device features causing a surface topography in said surface.

20. A particle treatment system, comprising:
a probe for contacting a surface of a patterned microstructure device;
a substrate holder for receiving said microstructure device;
a scan system operatively connected to said probe and said substrate holder, said scan system being adapted to position said probe on a surface portion of said microstructure device;
a particle pick up unit operatively connected to at least one of said probe and said substrate holder, said particle pick up unit being adapted to initiate adherence of a particle of interest to said probe and to move said particle from a first position on said surface portion of said microstructure device to a second position on said surface of said microstructure device that is spaced apart from said first position; and
an analysis system that is adapted to perform an analysis process on said particle of interest in the presence of at least a portion of said probe while said particle is in said second position.

21. The particle treatment system of claim 20, wherein said probe is configured to probe said surface of said microstructure device with sub-micrometer resolution.

22. The particle treatment system of claim 20, wherein said particle pick up unit is further adapted to move said particle of interest from said first position to a defined measurement environment, said defined measurement environment comprising at least one of a further surface portion of said microstructure device and a process chamber.

* * * * *